(12) United States Patent
Tokunaga et al.

(10) Patent No.: US 9,228,946 B2
(45) Date of Patent: Jan. 5, 2016

(54) ANALYZER, METHOD FOR DETERMINING A DISPENSED LIQUID AMOUNT, AND NON-TRANSITORY COMPUTER READABLE MEDIUM

(71) Applicant: Sysmex Corporation, Kobe-shi (JP)

(72) Inventors: Kazutoshi Tokunaga, Kobe (JP); Toshikatsu Fukuju, Kobe (JP); Tomoyuki Nishida, Kobe (JP); Hiroyuki Nishikawa, Kobe (JP); Keiji Tachibana, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 51 days.

(21) Appl. No.: 13/738,635

(22) Filed: Jan. 10, 2013

(65) Prior Publication Data

US 2013/0183198 A1 Jul. 18, 2013

(30) Foreign Application Priority Data

Jan. 16, 2012 (JP) ................................. 2012-006470

(51) Int. Cl.
*G01N 21/59* (2006.01)
(52) U.S. Cl.
CPC ...................... *G01N 21/59* (2013.01)
(58) Field of Classification Search
CPC ................................................... G01N 21/59
USPC ........................................ 422/68.1
See application file for complete search history.

(56) References Cited

U.S. PATENT DOCUMENTS

| | | | | |
|---|---|---|---|---|
| 4,180,085 A | * | 12/1979 | Berges et al. | 134/57 D |
| 7,704,457 B2 | * | 4/2010 | Patton | 422/63 |
| 2004/0023404 A1 | | 2/2004 | Shibata | |
| 2008/0131898 A1 | | 6/2008 | Tsuji et al. | |
| 2008/0241957 A1 | | 10/2008 | Shibata et al. | |
| 2009/0114255 A1 | * | 5/2009 | Kato | 134/56 R |
| 2009/0133512 A1 | * | 5/2009 | Kuroda | 73/863.01 |
| 2009/0254309 A1 | * | 10/2009 | Kubota et al. | 702/185 |
| 2010/0248293 A1 | | 9/2010 | Kuwano et al. | |

FOREIGN PATENT DOCUMENTS

| | | |
|---|---|---|
| EP | 2 023 145 A1 | 2/2009 |
| JP | 62-226059 A | 10/1987 |
| JP | 10-206212 A | 8/1998 |
| JP | 11-101798 A | 4/1999 |
| JP | 2004-108842 A | 4/2004 |
| JP | 2005-140615 A | 6/2005 |
| JP | 2006-292732 A | 10/2006 |
| JP | 2007-322244 A | 12/2007 |
| JP | 2010-169579 A | 8/2010 |
| JP | 2010-197047 A | 9/2010 |

OTHER PUBLICATIONS

Office Action from counterpart Chinese Application No. 201310013251.9, dated Nov. 11, 2013, 17 pages.

* cited by examiner

*Primary Examiner* — Shogo Sasaki
(74) *Attorney, Agent, or Firm* — Brinks Gilson & Lione

(57) ABSTRACT

An analyzer comprises a dispenser which dispenses a liquid into a container, a detector which comprises a phototransmitter which emits light to the container and a photoreceiver which receives light from the phototransmitter, a moving unit which changes a relative position between the container and the detector, and a controller which determines whether an amount of the liquid in the container is within a predetermined range, based on outputs from the detector at a plurality of the relative positions.

16 Claims, 11 Drawing Sheets

ANALYZER, METHOD FOR DETERMINING A DISPENSED LIQUID AMOUNT, AND NON-TRANSITORY COMPUTER READABLE MEDIUM

RELATED APPLICATIONS

This application claims priority under 35 U.S.C. §119 to Japanese Patent Application No. 2012-006470 filed on Jan. 16, 2012, the entire content of which is hereby incorporated by reference.

FIELD OF THE INVENTION

The present invention relates to analyzers, and in particular, to analyzers that include a dispenser which dispenses, into a container, a liquid to be used in analysis.

BACKGROUND OF THE INVENTION

There has been known an analyzer that includes a dispenser which dispenses, into a container, liquids such as a reagent and a sample (blood, urine, and the like) to be used by the analyzer, in which analyzer, the sample and the reagent are mixed together to prepare a measurement specimen, and analysis of components of the measurement specimen is performed.

The analyzer described in Japanese Patent Application Laid-open No. 2004-108842 includes a light source unit and a photometer which are fixedly provided at positions so as to face each other, while sandwiching therebetween a reaction container held by a reaction disc. The analyzer is configured such that the light source unit emits light to a reaction container held by the reaction disc, and light that has been transmitted through the reaction container enters the photometer, whereby it is detected whether a liquid specimen is present in the reaction container.

A measurement specimen to be measured by an analyzer is prepared by mixing reagents and a sample together. Therefore, when the amount of a reagent or the sample to be dispensed is too much or too small compared with a predetermined amount, the condition for preparing a measurement specimen fails to be constant, and thus, an accurate measurement result may not be obtained. Therefore, a technology is desired that monitors whether a liquid such as a reagent or a sample to be used by the analyzer has been dispensed by a predetermined amount. However, the above analyzer can merely detect whether a liquid is present in a container, and thus, there remains a problem that it cannot be determined whether the liquid has been dispensed by a predetermined amount.

SUMMARY OF THE INVENTION

The scope of the present invention is defined solely by the appended claims, and is not affected to any degree by the statements within this summary.

A first aspect of the present invention is an analyzer comprising a dispenser which dispenses a liquid into a container, a detector which comprises a phototransmitter which emits light to the container and a photoreceiver which receives light from the phototransmitter, a moving unit which changes a relative position between the container and the detector; and a controller which determines whether an amount of the liquid in the container is within a predetermined range, based on outputs from the detector at a plurality of the relative positions.

A second aspect of the present invention is a method for determining a dispensed liquid amount comprising dispensing a liquid into a container, changing a relative position between the container and a detector, which comprises a phototransmitter which emits light to the container and a photoreceiver which receives light from the phototransmitter, and determining whether an amount of the liquid in the container is within a predetermined range, based on outputs from the detector at a plurality of the relative positions.

A third aspect of the present invention is a non-transitory computer readable medium having computer instructions stored therein for causing a computer processor to perform predetermined operations comprising dispensing a liquid into a container, changing a relative position between the container and a detector, which comprises a phototransmitter which emits light to the container and a photoreceiver which receives light from the phototransmitter, and determining whether an amount of the liquid in the container is within a predetermined range, based on outputs from the detector at a plurality of the relative positions.

DETAILED DESCRIPTION OF THE PREFERRED EMBODIMENTS

The preferred embodiments of the present invention will be described hereinafter with reference to the drawings.

First, with reference to FIG. 1 to FIG. 7, a configuration of an immune analyzer 1 according to an embodiment of the present invention will be described. In the present embodiment, a case where the present invention is applied to the immune analyzer 1, which is an example of an analyzer, will be described.

The immune analyzer 1 according to an embodiment of the present invention is an apparatus that performs quantitative measurement or qualitative measurement on an antigen, an antibody, or the like contained in a sample such as blood (blood specimen) to be measured. The immune analyzer 1 is configured such that: a capture antibody (R1 reagent) that has been bound to an antigen contained in the sample (serum) is bound to magnetic particles (R2 reagent); then, complexes each composed of the antigen, the capture antibody, and the magnetic particles, which have been bound, are collected by using magnetism; and the R1 reagent containing the capture antibody that is unreacted (free) is removed (i.e., BF separation). Then, in the immune analyzer 1, the antigen that has been bound to the magnetic particles is bound to a labeled antibody (R3 reagent). Thereafter, complexes each composed of the magnetic particles, the antigen, and the labeled antibody, which have been bound, are collected by using magnetism, and the R3 reagent containing the labeled antibody that is unreacted (free) is removed (i.e., BF separation). Further, in the immune analyzer 1, a dispersion liquid (R4 reagent) and a luminescent substrate (R5 reagent), which emits light in a reaction process with the labeled antibody, are added in an R4/R5 reagent feeder 15. Thereafter, the amount of light generated by the reaction between the labeled antibody and the luminescent substrate is measured. Through this process, the immune analyzer 1 quantitatively measures the antigen which is contained in the sample and bound to the labeled antibody. It should be noted that the immune analyzer 1 is configured to be able to analyze a sample for a plurality of different analysis items.

Figure 1:
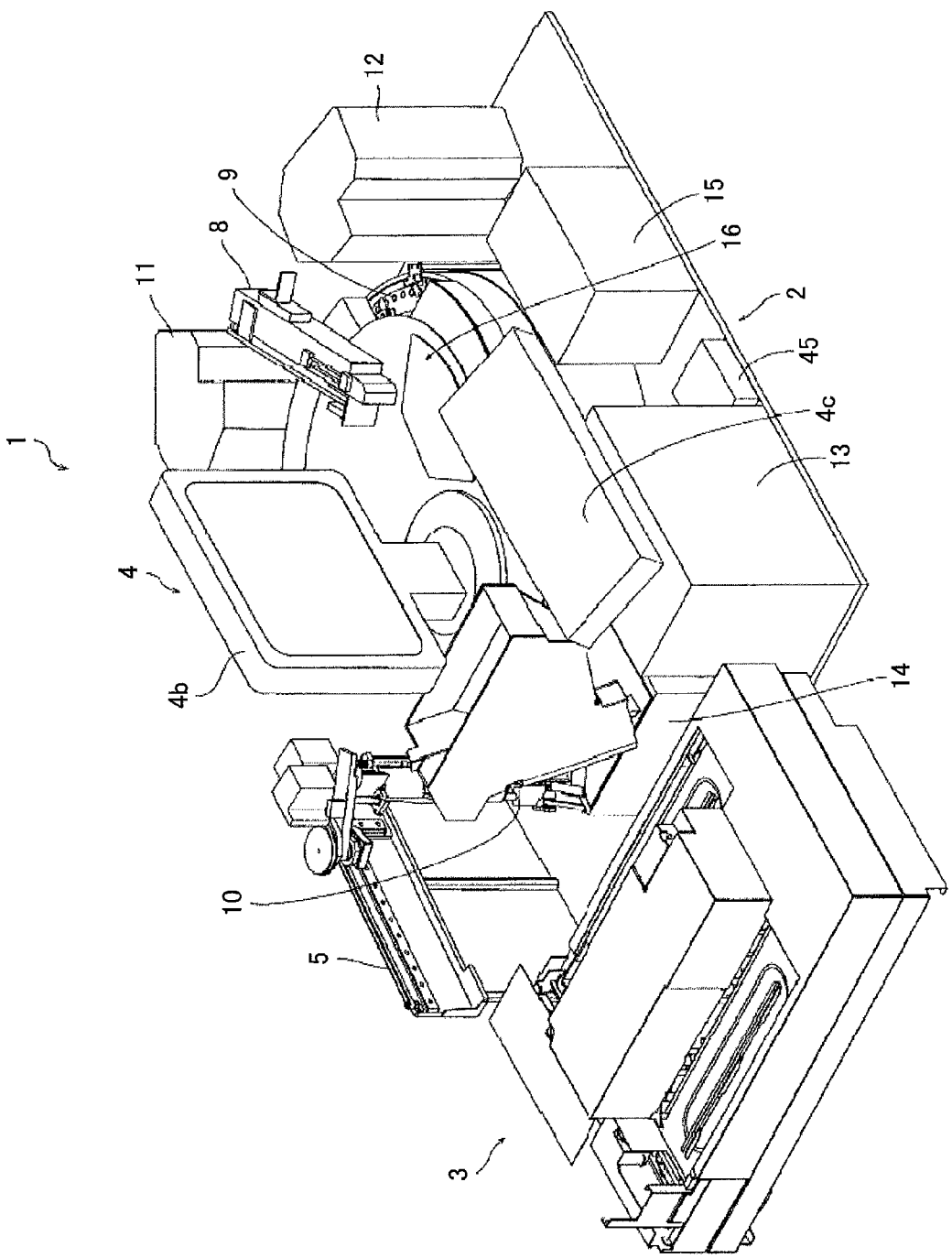
FIG. 1 is a perspective view showing an overall structure of an immune analyzer according to an embodiment of the present invention.
Figure 2:
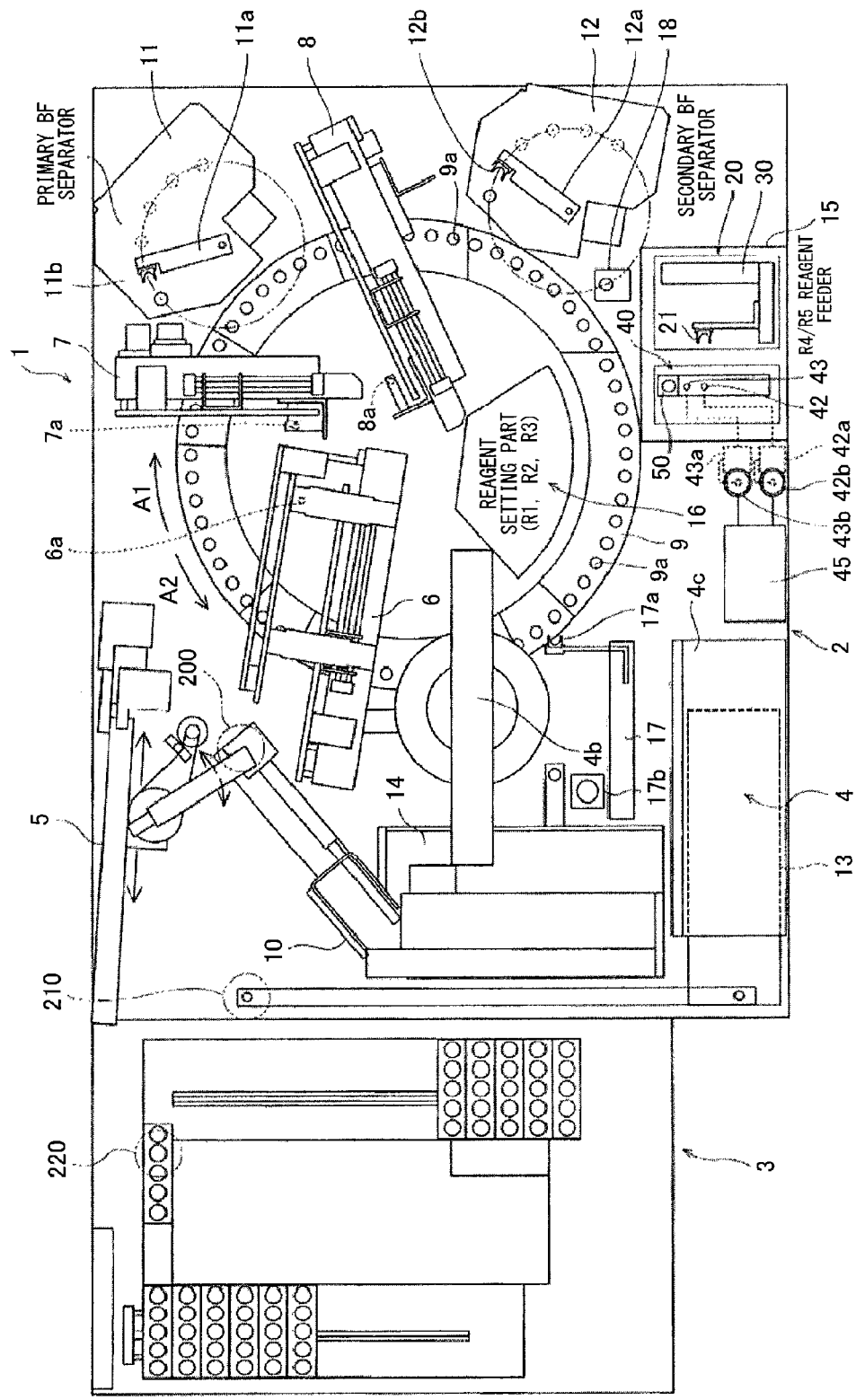
FIG. 2 is a plan view showing an overall structure of an immune analyzer according to an embodiment of the present invention.

As shown in FIG. 1 and FIG. 2, the immune analyzer 1 includes a measurement mechanism unit 2, a sample transporting unit (sampler) 3 arranged adjacent to the measurement mechanism unit 2, and a control apparatus 4 composed of a PC (personal computer) electrically connected to the measurement mechanism unit 2.

The sample transporting unit 3 is configured to be able to transport a rack on which a plurality of test tubes each containing a sample are placed. Further, the sample transporting unit 3 has a function of transporting a test tube containing a sample to a sample aspirating position 220 at which a sample dispensing arm 5 performs a sample aspirating operation.

Figure 3:
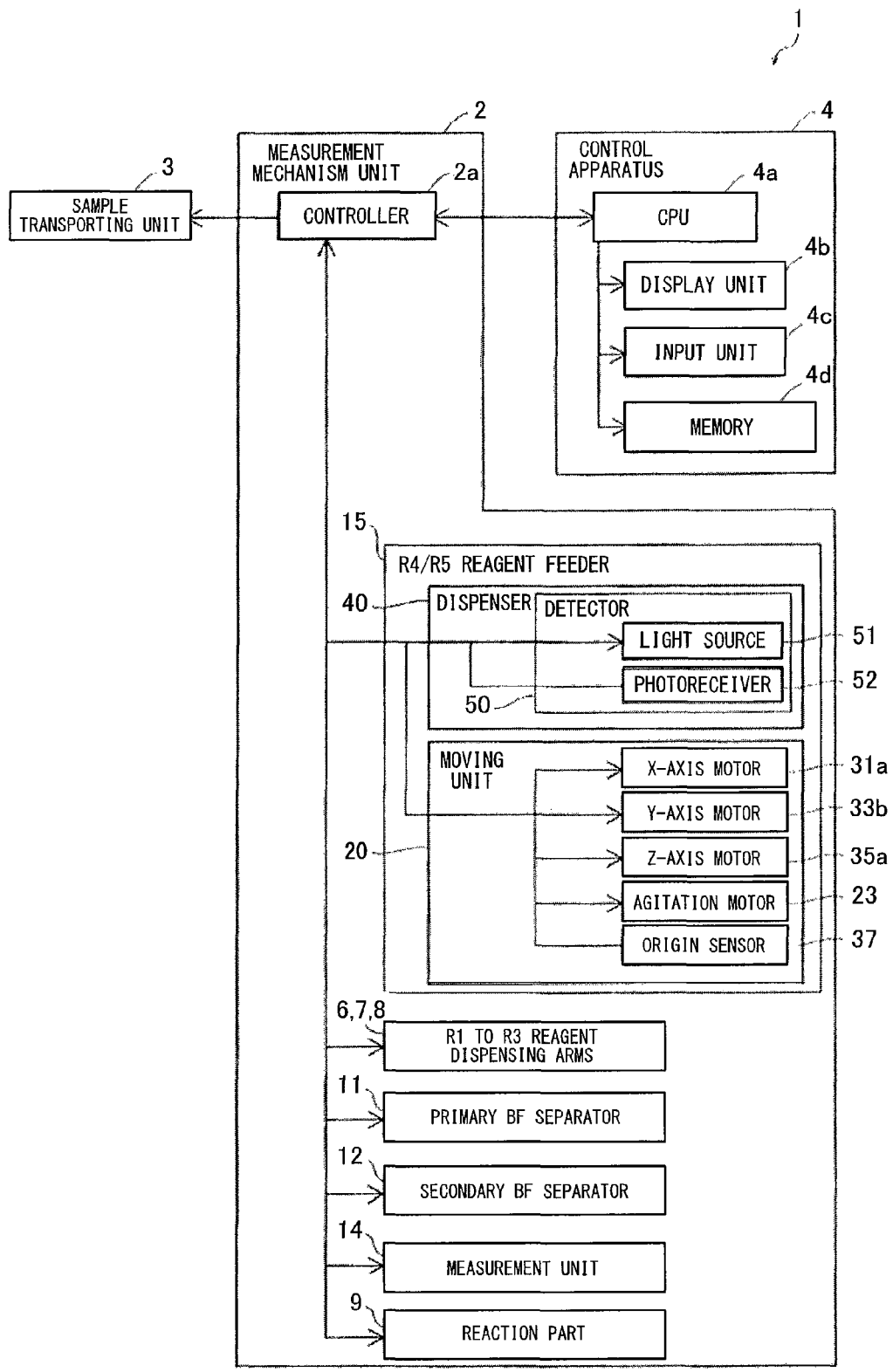
FIG. 3 is a block diagram for explaining a control configuration of an immune analyzer according to an embodiment of the present invention.

As shown in FIG. 3, the control apparatus 4 includes a CPU 4a, a display unit 4b, an input unit 4c, and a memory 4d. The CPU 4a has a function of analyzing a measurement result obtained by the measurement mechanism unit 2, and causing the display unit 4b to display the analysis result. Further, the memory 4d includes an HDD (hard disk drive), and is configured to store various programs and data of measurement results.

Further, as shown in FIG. 2, the measurement mechanism unit 2 includes the sample dispensing arm 5, an R1 reagent dispensing arm 6, an R2 reagent dispensing arm 7, an R3 reagent dispensing arm 8, a reaction part 9, a cuvette feeder 10, a primary BF separator 11, a secondary BF separator 12, a pipette tip feeder 13, a measurement unit 14, the R4/R5 reagent feeder 15, a reagent setting part 16, a cuvette transfer part 17, and an R4/R5 reagent container setting part 45.

As shown in FIG. 3, mechanism units (the reaction part 9, the R4/R5 reagent feeder 15, and the like) in the measurement mechanism unit 2 are controlled by a controller 2a provided in the measurement mechanism unit 2. A substrate having an FPGA or the like installed thereon is used for the controller 2a. Further, the controller 2a is communicably connected to the sample transporting unit 3 and the control apparatus 4, and has a function of receiving an operation instruction from the control apparatus 4, transmitting measurement result data to the control apparatus 4, transmitting an operation instruction to the sample transporting unit 3, and the like.

Figure 7:
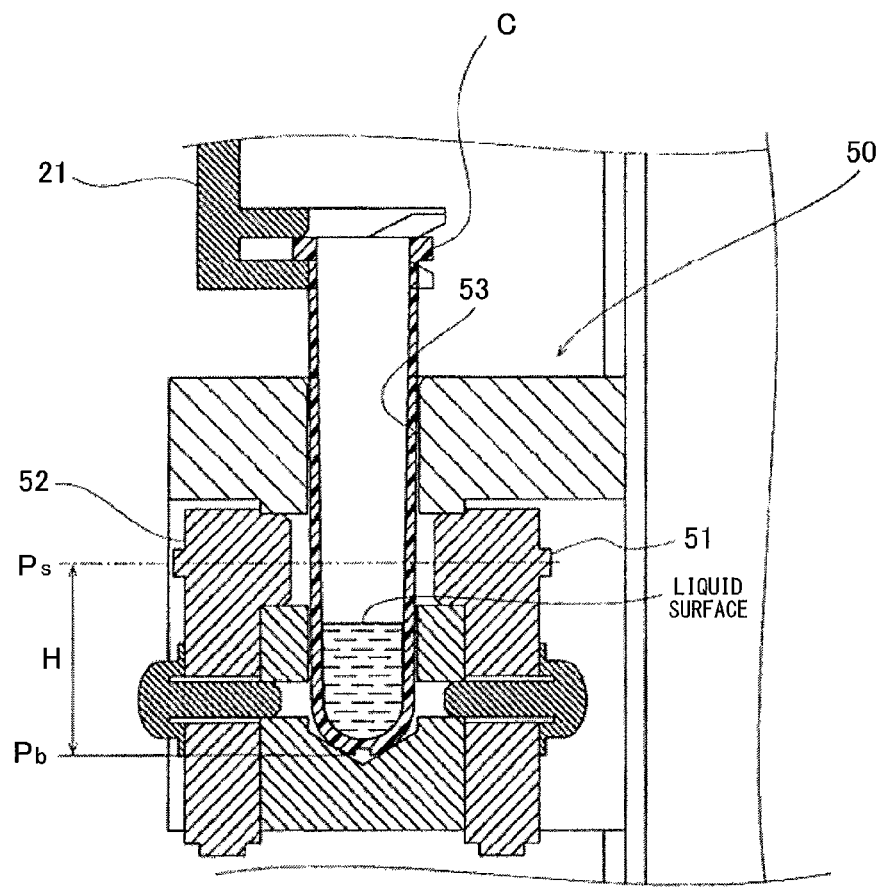
FIG. 7 is a cross section of a detector of the R4/R5 reagent feeder shown in FIG. 4.

The cuvette feeder 10 shown in FIG. 2 is configured to be able to accommodate a plurality of cuvettes C (see FIG. 7), and has a function of sequentially supplying cuvettes C, one by one, to a sample discharging position 200 at which the sample dispensing arm 5 performs a sample dispensing operation. As shown in FIG. 7, each cuvette C is a container having an elongated cylindrical shape, whose upper end is open, whose lower end is formed as a round bottom, and whose inner lateral surface and outer lateral surface are circular in a horizontal cross section. The cuvette C is a reaction container into which a measurement specimen prepared from a sample and reagents is dispensed. The cuvette C is provided with, at an upper end portion thereof, a flange protruding outward from the outer lateral surface thereof so as to allow catchers provided at positions in the measurement mechanism unit 2 to grip the cuvette C.

As shown in FIG. 2, the R1 reagent dispensing arm 6 is configured to aspirate the R1 reagent, by using a pipette 6a, from an R1 reagent container set in the reagent setting part 16, and to dispense (discharge) the aspirated R1 reagent into a cuvette C placed at the sample discharging position 200. Further, the R1 reagent dispensing arm 6 has a function of transferring the cuvette C placed at the sample discharging position 200 to the reaction part 9, by using a catcher (not shown).

The pipette tip feeder 13 has a function of transporting, one by one, a plurality of pipette tips that have been fed therein to a tip attaching position 210 at which the sample dispensing arm 5 performs a tip attaching operation.

The sample dispensing arm 5 is configured to be movable. The sample dispensing arm 5 has a function of aspirating, after a pipette tip is attached to the sample dispensing arm 5 at the tip attaching position 210, a sample in a test tube that has been transported to the sample aspirating position 220 by the sample transporting unit 3, and dispensing (discharging) the sample into the cuvette C at the sample discharging position 200 into which the R1 reagent has been dispensed by the R1 reagent dispensing arm 6.

The R2 reagent dispensing arm 7 is configured to aspirate the R2 reagent by using a pipette 7a from an R2 reagent container set in the reagent setting part 16, and to dispense (discharge) the aspirated R2 reagent into the cuvette C containing the R1 reagent and the sample.

The reaction part 9 is formed, when seen in a plan view, in a substantially annular shape so as to surround the reagent setting part 16 which has a substantially round shape. Further, the reaction part 9 is configured to be rotatable and has a function of moving a cuvette C held in a cuvette holder (hole) 9a to various process positions at each of which a corresponding process (dispensing of a reagent, or the like) is performed. Specifically, the reaction part 9 is rotated in an arrow A1 direction, to transport the cuvette C that has been transferred to the reaction part 9 by the R1 reagent dispensing arm 6, to respective process positions for the R2 reagent dispensing arm 7, the primary BF separator 11, the R3 reagent dispensing arm 8, the secondary BF separator 12, and the R4/R5 reagent feeder 15, in this order, and then, to transfer the cuvette C to the measurement unit 14.

The primary BF separator 11 is configured to take out the cuvette C containing the sample, the R1 reagent, and the R2 reagent, out of the reaction part 9 by using a catcher 11b of a transfer arm 11a, and to perform a BF separation process for separating the R1 reagent that is unreacted (unnecessary component) from the magnetic particles in the specimen in the cuvette C. The primary BF separator 11 is configured to return, after completing the BF separation process, the cuvette C to the reaction part 9 by using the catcher 11*b* of the transfer arm 11*a*.

The R3 reagent dispensing arm 8 is configured to aspirate the R3 reagent by using a pipette 8*a* from an R3 reagent container set in the reagent setting part 16. Further, the R3 reagent dispensing arm 8 is configured to dispense (discharge) the aspirated R3 reagent into the cuvette C containing the specimen after the BF separation performed by the primary BF separator 11.

The secondary BF separator 12 is configured to obtain the cuvette C containing the specimen after the (primary) BF separation performed by the primary BF separator 11 and the R3 reagent, from the reaction part 9 by using a catcher 12*b* of a transfer arm 12*a*, and to perform a (secondary) BF separation process for separating the R3 reagent that is unreacted (unnecessary component) from the magnetic particles in the specimen in the cuvette. Further, the secondary BF separator 12 is configured to transfer the cuvette C after the BF separation process to a setting part 18, by using the catcher 12*b* of the transfer arm 12*a*.

The R4/R5 reagent feeder 15 includes a moving unit 20 which transfers a cuvette C, and a dispenser 40 which sequentially dispenses the R4 reagent and the R5 reagent into the cuvette C containing the specimen after the BF separation process performed by the secondary BF separator 12. The cuvette C into which the R4 reagent and the R5 reagent have been dispensed is returned to the reaction part 9 by the moving unit 20. A detailed configuration of the R4/R5 reagent feeder 15 will be described later.

The measurement unit 14 is provided in order to measure the amount of the antigen contained in the sample, by obtaining, by means of a photomultiplier tube, light that is generated in the reaction process between the luminescent substrate and the labeled antibody bound to the antigen in the sample on which various processes have been performed. It should be noted that the cuvette C is taken out of the reaction part 9 by the cuvette transfer part 17 having a catcher 17*a*, and is set in the measurement unit 14. In addition to the function of transferring the cuvette C to the measurement unit 14, the cuvette transfer part 17 has a function of transferring the cuvette C to a disposal part 17*b* to discard the cuvette C.

The reagent setting part 16 is provided in order to set thereon a plurality of R1 reagent containers each containing the R1 reagent containing the capture antibody, a plurality of R2 reagent containers each containing the R2 reagent containing the magnetic particles, and a plurality of R3 reagent containers each containing the R3 reagent containing the labeled antibody.

Next, the configuration of the R4/R5 reagent feeder 15 will be described in detail.

Figure 4:
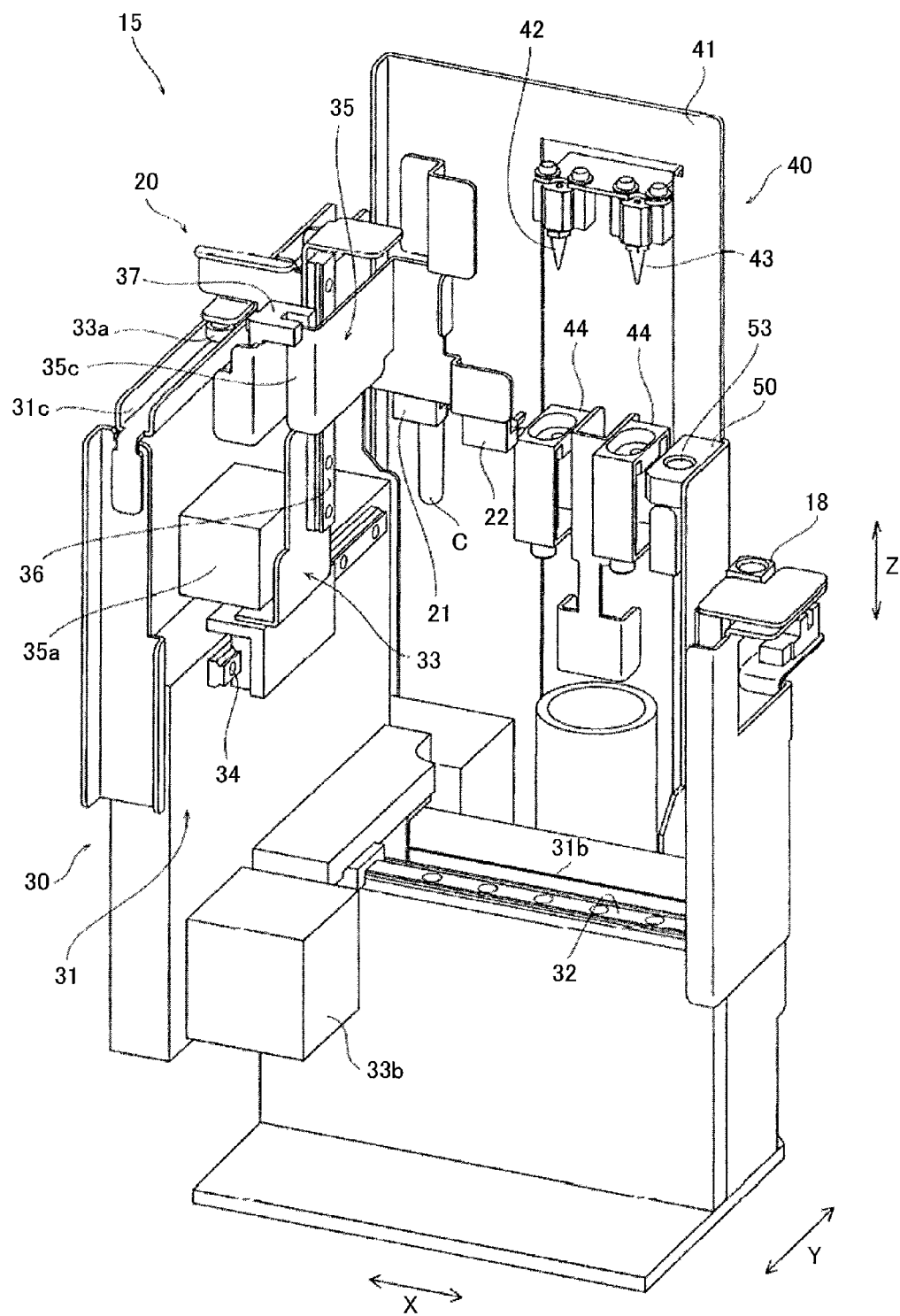
FIG. 4 is a schematic perspective view for explaining a configuration of an R4/R5 reagent feeder of an immune analyzer according to an embodiment of the present invention.
Figure 5:
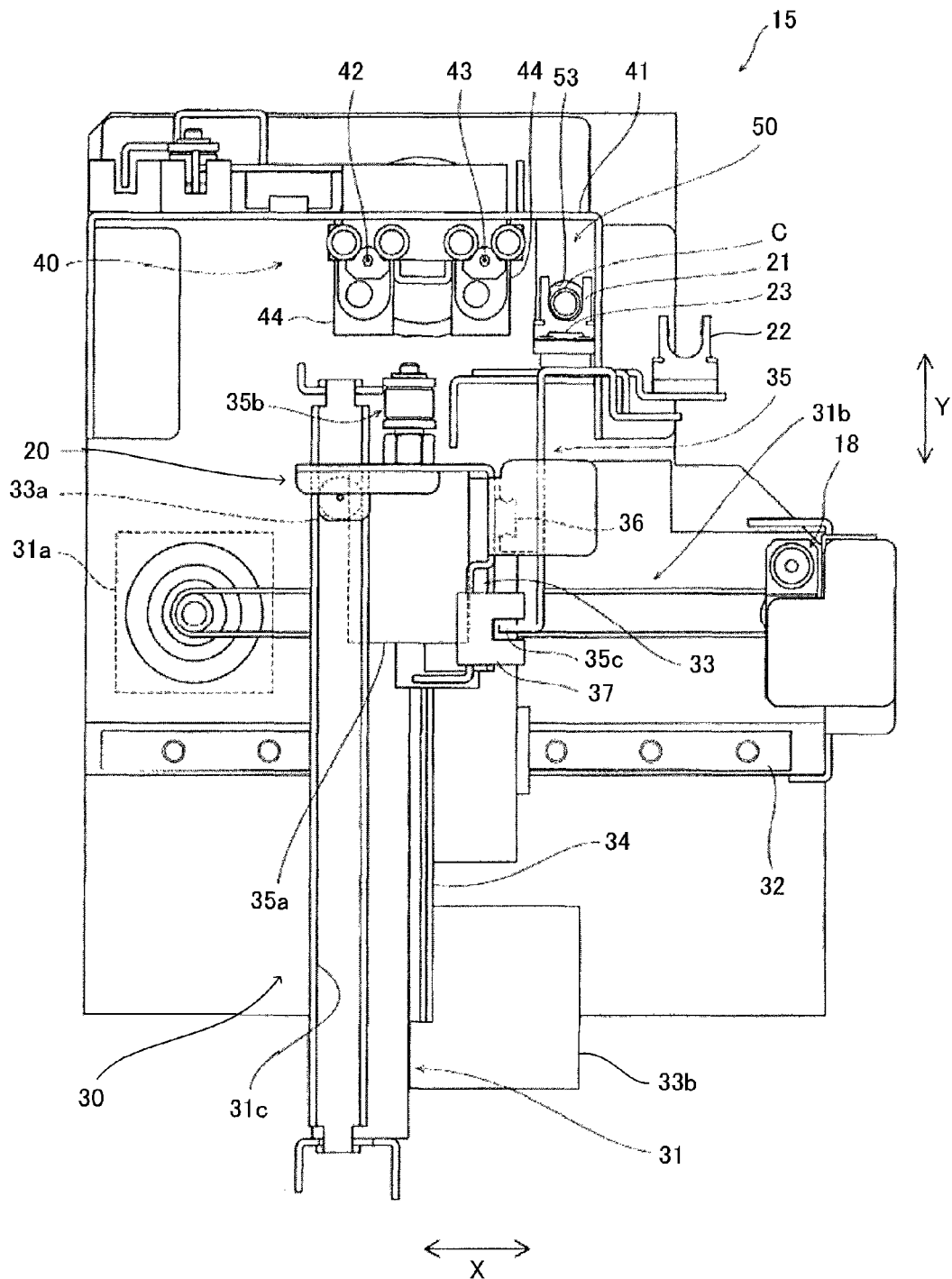
FIG. 5 is a schematic plan view of the R4/R5 reagent feeder shown in FIG. 4.
Figure 6:
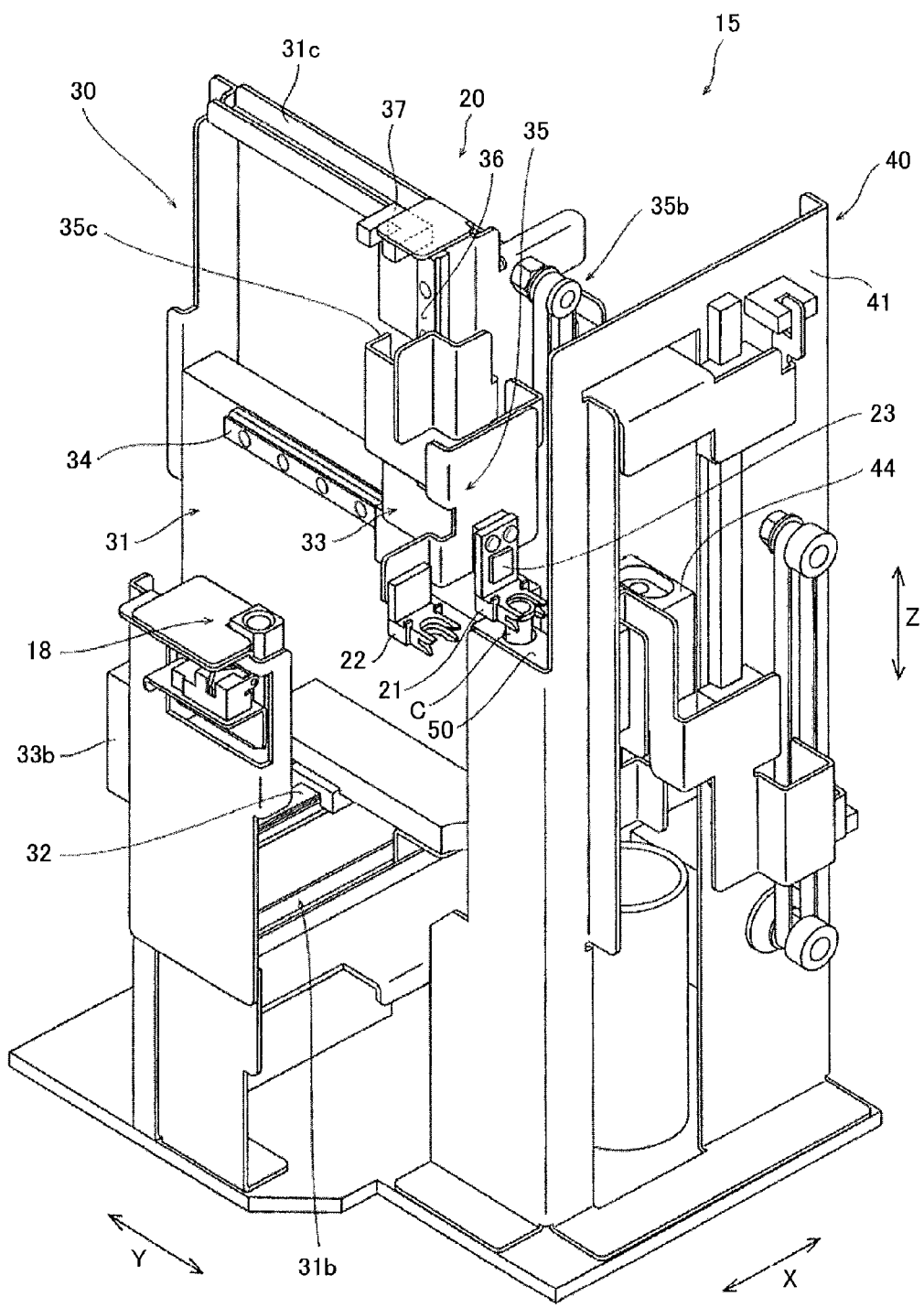
FIG. 6 is a schematic perspective view of the R4/R5 reagent feeder shown in FIG. 4, viewed from another angle.

As shown in FIG. 4 to FIG. 6, the moving unit 20 and the dispenser 40 of the R4/R5 reagent feeder 15 are arranged so as to face each other in the Y direction. The moving unit 20 includes two catchers 21 and 22, and a moving mechanism 30 for moving the two catchers 21 and 22. The dispenser 40 includes dispensing nozzles 42 and 43 which are fixedly provided on a side of a frame 41 that faces the moving unit 20, cleaning parts 44 respectively provided below the dispensing nozzles 42 and 43, and a detector 50 for detecting a liquid (R4/R5 reagent) in a cuvette C held by the catcher 21.

The moving mechanism 30 of the moving unit 20 is a moving mechanism that is movable along three orthogonal axes, that is, along the horizontal directions (the X direction and the Y direction orthogonal to each other in a horizontal plane) and the up-down direction (the Z direction). Specifically, the moving mechanism 30 includes a first frame 31 movably supported on a guide rail 32 which extends in the X direction, a second frame 33 which movably engages a guide rail 34 which is provided on the first frame 31 so as to extend in the Y direction, a third frame 35 which movably engages a guide rail 36 which is provided on the second frame 33 so as to extend in the Z direction.

As shown in FIG. 4, the first frame 31 is a plate-like frame that extends in the Y-Z directions, and is configured to be movable in the X direction along the guide rail 32 by an X-axis motor 31*a* which drives a belt-pulley mechanism 31*b* (see FIG. 5).

The second frame 33 is formed so as to extend in the up-down direction (the Z direction). The second frame 33 is supported, at its lower end portion, by the first frame 31 via the guide rail 34, and engages, at its upper end portion, a guide groove 31*c* provided on the first frame 31 and extending in the Y direction, by means of a guide roller 33*a*. The second frame 33 is configured to be movable in the Y direction along the guide rail 34 by a belt-pulley mechanism (not shown) being driven by a Y-axis motor 33*b* provided on the first frame 31.

The third frame 35 is movably supported by the second frame 33 via the guide rail 36. The third frame 35 is configured to be movable in the up-down direction (the Z direction) along the guide rail 36, by a belt-pulley mechanism 35*b* (see FIG. 5) being driven by a Z-axis motor 35*a* provided on the second frame 33. At an edge of the third frame 35 (the edge in the Y direction), the two catchers 21 and 22 are provided so as to protrude toward the dispenser 40.

The Z-axis motor 35a is implemented by a pulse motor, and is configured to be driven by pulse signal control from the controller 2*a* of the measurement mechanism unit 2. It should be noted that a transmissive-type origin sensor 37 is fixedly set at a predetermined position in an upper end portion of the second frame 33. The origin sensor 37 has a function of detecting a predetermined portion (a detection piece 35*c*) of the third frame 35 and positioning an origin position Po for the catchers 21 and 22 (the third frame 35).

As shown in FIG. 6, the catcher 21 is configured to be able to grip (hold) a cuvette C, by sandwiching the flange at the upper end of the cuvette C by means of a pair of claws. Further, the catcher 21 is provided with an agitation motor (vibrating motor) 23, and is configured to be able to agitate the liquid in the cuvette C by the agitation motor 23 vibrating the catcher 21. It should be noted that the catcher 22 is a spare catcher, and is used, for example, when there is abnormality in the apparatus.

Through the above configuration, the moving unit 20 is configured to be able to transfer the cuvette C, by moving the catcher 21 to the respective positions corresponding to the setting part 18, the dispensing position of the dispensing nozzles 42 and 43, the detector 50, and the reaction part 9 (cuvette return position).

As shown in FIG. 4, the dispensing nozzles 42 and 43 of the dispenser 40 are set at positions near an upper end portion of the frame 41, with their tips (discharge openings) facing downward. As shown in FIG. 2, the dispensing nozzles 42 and 43 are respectively in fluid communication with R4 and R5 reagent containers in the R4/R5 reagent container setting part 45, via syringe pumps 42*a* and 43*a* and reagent chambers 42*b* and 43*b*. The R4 and R5 reagents in the R4 and R5 reagent containers in the R4/R5 reagent container setting part 45 are temporarily stored in the reagent chambers 42*b* and 43*b* respectively, and are measured by predetermined amounts through operations by the corresponding syringe pumps 42*a* and 43*a* to be discharged from the dispensing nozzles 42 and 43, respectively.

As shown in FIG. 4, the two cleaning parts 44 are configured be movable in the up-down direction (the Z direction) and have a function of ascending up to the tip positions of the dispensing nozzles 42 and 43 to clean the nozzle tip portions, respectively.

The detector 50 is an optical detector having a light source 51 and a photoreceiver 52 (see FIG. 7), and is fixedly attached to the frame 41. The detector 50 is provided in order to detect a liquid (R4/R5 reagent) in a cuvette C inserted in a hole portion 53. It should be noted that FIG. 5 and FIG. 6 each show a state where a cuvette C gripped by the catcher 21 is inserted in the hole portion 53.

As shown in FIG. 7, the light source 51 and the photoreceiver 52 are arranged so as to face each other, sandwiching therebetween the hole portion 53 which extends in the up-down direction in the detector 50. The light source 51 is configured to emit light to a lateral face of a cuvette C inserted in the hole portion 53. The photoreceiver 52 is configured to receive light that has been emitted by the light source 51 and has been transmitted through the cuvette C, and to output an analog signal to the controller 2a at a signal strength (output voltage) corresponding to the amount of the transmitted light that has been received (transmitted light intensity).

Further, a sensor position (the position at the height of the optical axis between the light source 51 and the photoreceiver 52) Ps is set at a position at a height H from a sensor adjustment position Pb which corresponds to the bottom of the hole portion 53 and at which a detection operation is started. The sensor position Ps is set at such a position where, when a cuvette C in which the R4/R5 reagent having a normal amount has been dispensed (the lower end of the cuvette C) is located at the sensor adjustment position Pb, the liquid surface of the R4/R5 reagent in the cuvette C is lower than the sensor position Ps.

According to the above configuration, in the R4/R5 reagent feeder 15, the moving unit 20 takes out a cuvette C set at the setting part 18 by gripping it by means of the catcher 21, and locates the cuvette C below the dispensing nozzle 42 (43), and the dispenser 40 causes the dispensing nozzle 42 (43) to discharge a corresponding reagent, whereby a dispensing operation of the R4 (R5) reagent is performed. Further, the R4/R5 reagent feeder 15 is configured such that after the cuvette C into which the R4 and R5 reagents have been dispensed is inserted in the detector 50, the cuvette C is caused to ascend from the sensor adjustment position Pb, whereby a liquid detecting operation is performed in which the detector 50 and the cuvette C are moved relative to each other in the up-down direction. In the present embodiment, the controller 2a of the measurement mechanism unit 2 is configured to measure the time period (detection time period T), during which the signal strength (output voltage) is lower than a threshold value Th, based on an output from the detector 50 (the photoreceiver 52) in this liquid detecting operation.

Next, with reference to FIG. 8, measurement of the detection time period T performed by the controller 2a of the measurement mechanism unit 2 will be described in detail.

The liquid (R4/R5 reagent) contained in the cuvette C during the detection is in a state where the complexes each composed of the magnetic particles, the antigen, and the labeled antibody are dispersed in the liquid. Thus, when light is transmitted through this liquid (R4/R5 reagent), the amount of the transmitted light is greatly reduced. Therefore, by setting the threshold value Th to a predetermined signal strength between: a signal strength (output voltage) from the photoreceiver 52 at the time when light has passed through the space in a cuvette C where the R4/R5 reagent is not present; and a signal strength from the photoreceiver 52 at the time when light has been transmitted through the R4/R5 reagent in a cuvette C, it is possible to detect whether the liquid (R4/R5 reagent) is present in the cuvette C, based on whether an output voltage from the photoreceiver 52 is lower than the threshold value Th.

Figure 8:
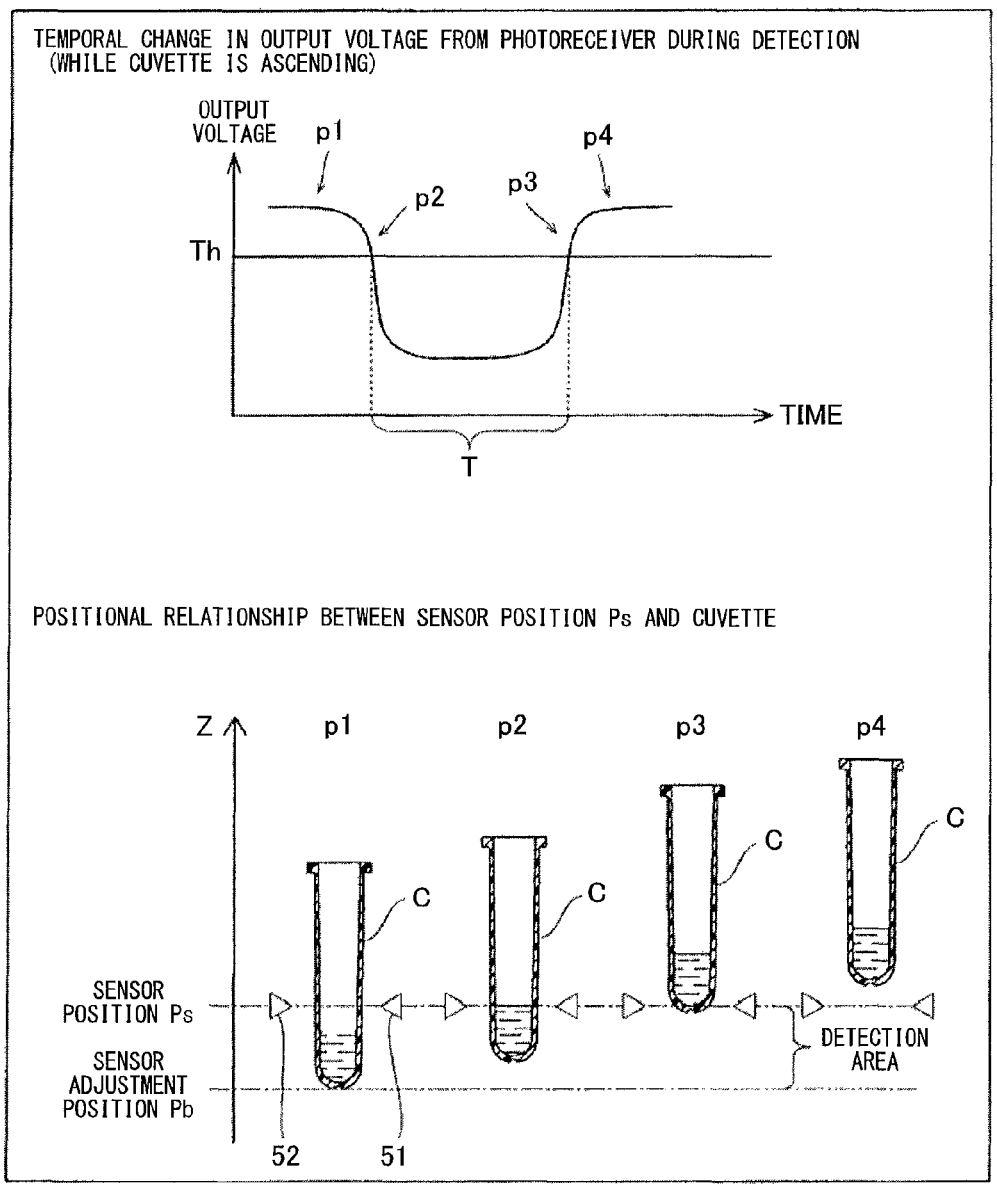
FIG. 8 illustrates a change in an output voltage from a photoreceiver during detection of a liquid amount performed by a detector.

When a cuvette C is caused to ascend during detection from the sensor adjustment position Pb at which is the detection is started, the output voltage from the photoreceiver 52 changes as shown in FIG. 8 due to the relative movement in the up-down direction between the cuvette C and the detector 50 (the photoreceiver 52). Specifically, at a position p1 where the ascent is started and the liquid surface is lower than the sensor position Ps, the output voltage from the photoreceiver 52 is greater than the threshold value Th. At a position p2 where the liquid surface reaches the sensor position Ps as a result of the ascent of the cuvette C, the output voltage from the photoreceiver 52 decreases and becomes lower than the threshold value Th (the R4/R5 reagent is detected). The state where the output voltage is lower than the threshold value Th continues to a position p3 where the lower end of the liquid in the cuvette C passes the sensor position P. After the lower end of the liquid in the cuvette C passes the position p3, the output voltage from the photoreceiver 52 increases and exceeds the threshold value Th. Accordingly, at a position p4 where the position of the lower end of the liquid in the cuvette C is higher than the sensor position Ps, the output voltage from the photoreceiver 52 becomes greater than the threshold value Th as in the case of the position p1.

From this output voltage waveform, it is known that the time period (the detection time period T) during which the output voltage is lower than the threshold value Th reflects the amount of the liquid in the cuvette C. That is, when the amount of the liquid in the cuvette C is large, the detection time period T becomes long, and when the amount of the liquid in the cuvette C is small, the detection time period T becomes short.

Therefore, in the present embodiment, the controller 2a causes the moving unit 20 to move the cuvette C upward relative to the detector 50 at a substantially constant speed, and measures the time period (the detection time period T) during which the output voltage has been lower than the threshold value Th during the ascent. Then, the CPU 4a of the control apparatus 4 determines whether the amount of the liquid (R4/R5 reagent) in the cuvette C is within a predetermined normal range, based on whether the detection time period T is within a predetermined detection time period range. Accordingly, different from a detection method that detects the amount of a liquid by causing a probe to contact the liquid surface, it is possible to detect the amount of a liquid in the cuvette C without contacting the liquid surface. Therefore, it is possible to perform liquid amount detection while preventing occurrence of carry-over of a measurement specimen to a different cuvette C.

In the present embodiment, it is configured such that a liquid (reagent) is contained in a cuvette C by 150 μL=R4 reagent 50 μL+R5 reagent 100 μL during liquid amount detection. Therefore, in consideration of a variation (variation within a normal range) in the dispensed amount by the dispenser 40, 150 μL±5% (142.5 μL<liquid amount<157.5 μL) is set as the normal range for the liquid amount during the detection. A detection time period when a cuvette C contains the liquid having an upper limit amount (157.5 μL), which is higher than the normal range of the liquid amount, is set as an upper limit time period T1. A detection time period when a cuvette C contains the liquid having a lower limit amount (142.5 μL), which is lower than the normal range, is set as a lower limit time period T2. When the detection time period T is within the predetermined detection time period range (T2<T<T1), that is, between the upper limit time period T1 and the lower limit time period T2, the CPU 4a determines that the amount of the liquid in the cuvette C is within the predetermined normal range. On the other hand, when the detection time period T is shorter than or equal to T2 (T≤T2), or when the detection time period T is longer than or equal to T1 (T1≤T), the CPU 4a determines that the liquid amount is outside the normal range (constant amount abnormality).

When it has been determined that the liquid amount is outside the normal range (constant amount abnormality), it is conceivable that there is abnormality in the apparatus, and thus, the next dispensing operation (the cuvette C to be subjected to the next dispensing) and thereafter are stopped at this time point. Further, the display unit 4b of the control apparatus 4 displays an indication that an R4/R5 reagent constant amount abnormality error has occurred, whereby the user is notified of the abnormality.

However, even when it has been determined that the liquid amount is outside the normal range (constant amount abnormality), it is possible to normally perform measurement on a cuvette C for which liquid amount detection has been performed before that time point and the liquid amount has been determined as being within the normal range. Therefore, in the present embodiment, with respect to the cuvette C for which it has been determined that there is abnormality, a process of attaching an abnormality flag is performed on a measurement program. Then, the measurement unit 14 confirms the flag before performing the measurement process, and with respect to a cuvette C (without the abnormality flag) for which liquid amount detection was already performed before the determination that there is abnormality has been made, the measurement unit 14 performs the measurement process, but with respect to the cuvette C with the abnormality flag, the measurement unit 14 does not perform the measurement process.

Next, with reference to FIG. 4, FIG. 8, and FIG. 9, a movement condition for the catcher 21 during the detection operation will be described.

In the present embodiment, when the catcher 21 is moved in the up-down direction in accordance with the liquid detecting operation performed in the detector 50, the moving unit 20 (the Z-axis motor 35a) is driven on different movement conditions under control by the controller 2a, that is, the moving unit 20 is driven differently between: a period in which the catcher 21 is ascending and liquid amount detection is included; and a period in which the catcher 21 is descending in order to locate the cuvette C at the sensor adjustment position Pb.

Figure 9:
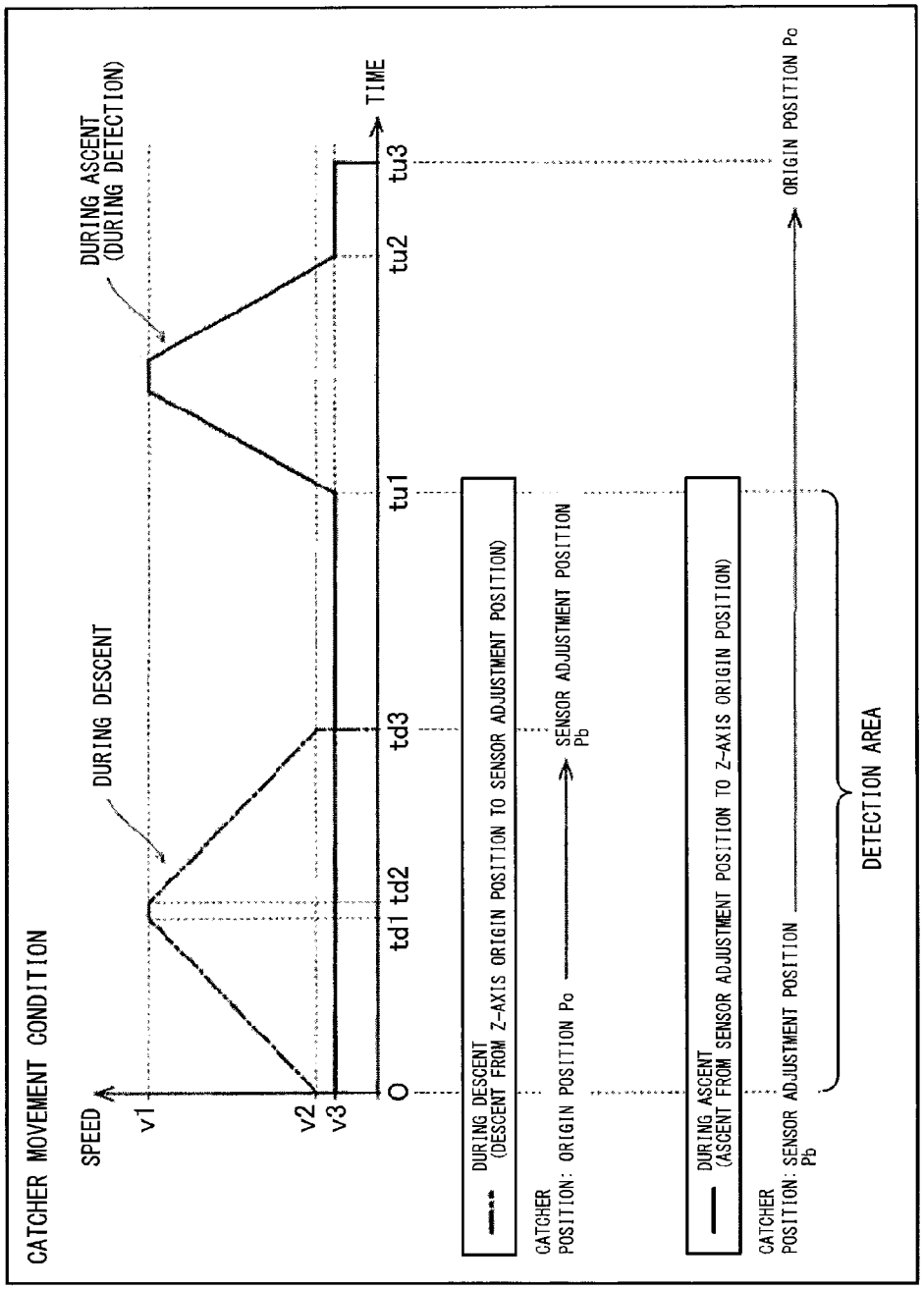
FIG. 9 illustrates a movement condition for a catcher during detection of a liquid amount performed by a detector.

As shown in FIG. 9, while the catcher 21 is descending (see the two-dot chain line) from the origin position Po as the detection position for the origin sensor 37 (see FIG. 4) to the sensor adjustment position Pb inside the detector 50, the speed of the catcher 21 is accelerated from speed v2 to speed v1 from the time when the catcher 21 starts descending till time td1, and the catcher 21 descends at the constant speed v1 from time td1 till time td2. Then, the speed of the catcher 21 is reduced to speed v2 from time td2 till time td3, and at time td3, the cuvette C reaches the sensor adjustment position Pb, when the moving unit 20 (the catcher 21) is stopped. As apparent from FIG. 9, during the descent, the catcher 21 is moved (descends) at a higher average speed than that during the ascent to be described below, and thus, the descending movement of the catcher 21 from the origin position Po to the sensor adjustment position Pb is performed rapidly in a short time period.

On the other hand, during the ascent from the sensor adjustment position Pb to the origin position Po, the catcher 21 is moved at a constant speed v3 (<v2) from the time when the catcher 21 starts ascending till time tu1. While moving at the constant speed (speed v3) till time tu1, the cuvette C passes the detection area from the position p1 to position p3 in FIG. 8. That is, the liquid in the cuvette C passes the sensor position Ps of the detector 50 at the constant speed v3, and during this period, the detection time period T is measured by the controller 2a. As shown in FIG. 9, during the period from time tu1 to time tu2 after the detection, a trapezoid drive is performed that includes acceleration from speed v3 to speed v1 and deceleration from speed v1 to speed v3. Thus, the catcher 21 is moved at a low speed of the constant speed v3 during the liquid detecting operation, and after the liquid detection, the catcher 21 is accelerated and is rapidly moved toward the origin position Po. From time tu2, the catcher 21 ascends at the constant speed v3 again and reaches the origin position Po (detected by the origin sensor 37) at time tu3, positioning of the origin position is performed, and the catcher 21 is stopped.

Next, with reference to FIG. 2 and FIG. 10, a measurement process operation performed by the immune analyzer 1 (the measurement mechanism unit 2) according to an embodiment of the present invention will be described. The measurement process operation is started based on a start instruction from the control apparatus 4, and operation control is performed by the controller 2a of the measurement mechanism unit 2. Specifically, the controller 2a performs step S1 to step S9, step S13 to step S19, and step S21 to step S28 of step S10, and the CPU 4a performs step S11, step S12, and step S29 to step S33 of step S10.

Figure 10:
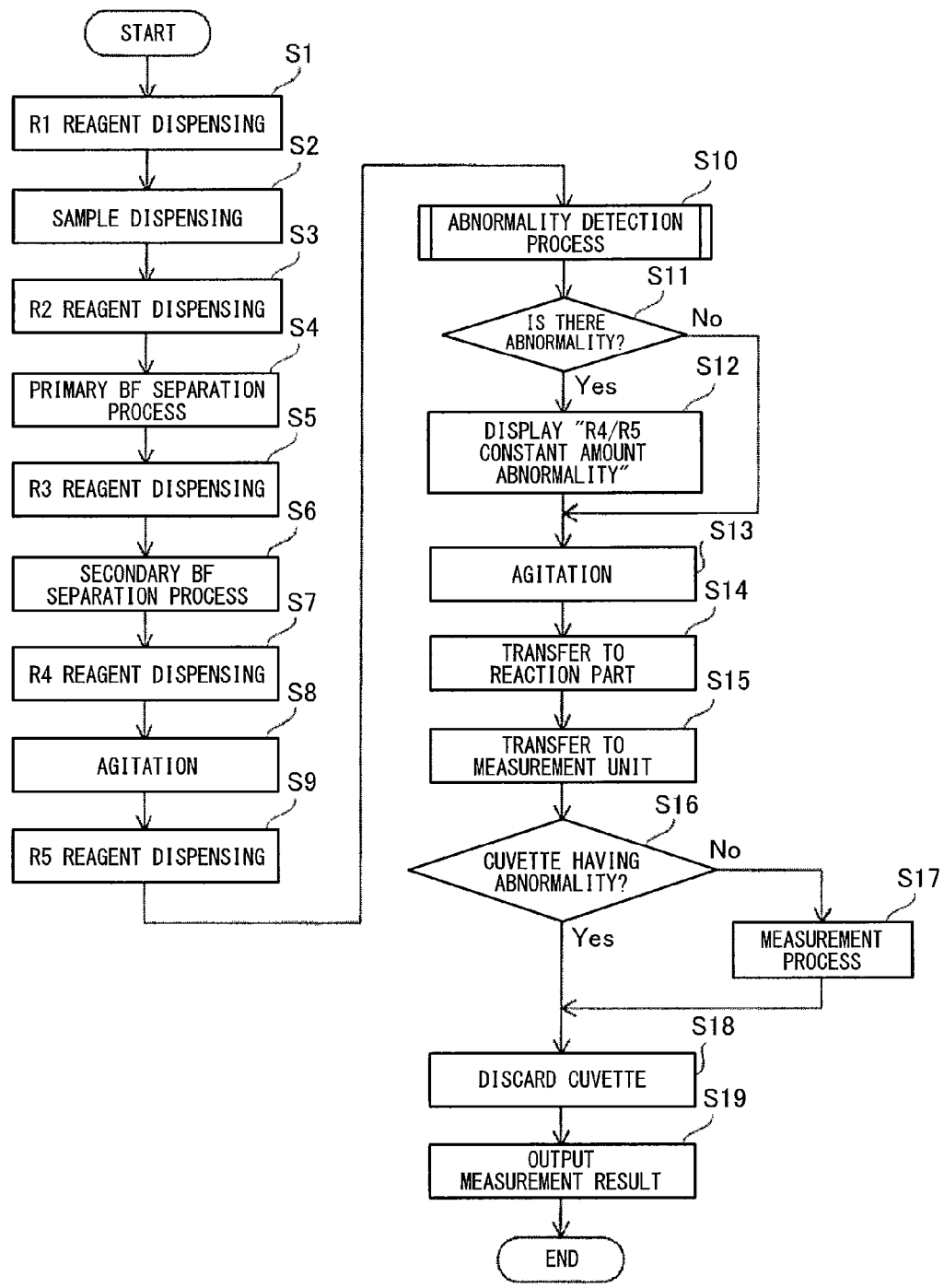
FIG. 10 is a flow chart for explaining a measurement process operation performed by an immune analyzer according to an embodiment of the present invention.

First, as shown in FIG. 2 and FIG. 10, in step S1, the R1 reagent is dispensed by the R1 reagent dispensing arm 6 into a cuvette C supplied at the sample discharging position 200 by the cuvette feeder 10 (see FIG. 2).

In step S2, the sample dispensing arm 5 to which a pipette tip is attached at the tip attaching position 210 aspirates a sample at the sample aspirating position 220 (see FIG. 2), and dispenses the sample into the cuvette C into which the R1 reagent has been dispensed at the sample discharging position 200. After the sample has been dispensed, the cuvette C is set in the reaction part 9 (cuvette holder 9a) by the catcher of the R1 reagent dispensing arm 6. The reaction part 9 transports the cuvette C by rotating in the A1 direction.

In step S3, the R2 reagent is dispensed by the R2 reagent dispensing arm 7 into the cuvette C set in the reaction part 9. After the R2 reagent has been dispensed, when the cuvette C is transported to a predetermined taking-out position, the cuvette C is taken out of the reaction part 9 by the transfer arm 11a (the catcher 11b) of the primary BF separator 11. Then, in step S4, a primary BF separation process is performed by the primary BF separator 11.

In the primary BF separation process, a BF cleaning process including attraction of the magnetic particles in the specimen contained in the cuvette C, aspiration of the liquid (unnecessary component), discharge of a cleaning solution, and an agitation operation is repeated three times, and finally, an aspiration process in which the magnetic particles in the cuvette C are attracted and the cleaning solution is aspirated is performed. As a result, the R1 reagent that is unreacted (unnecessary component) is separated from the magnetic particles in the specimen in the cuvette C (BF separation). After the primary BF separation process ends, the cuvette C is returned to the reaction part 9 by the transfer arm 11a (the catcher 11b).

In step S5, the R3 reagent is dispensed by the R3 reagent dispensing arm 8 into the cuvette C returned to the reaction part 9. In step S6, the cuvette C is taken out of the reaction part 9 by the transfer arm 12a (the catcher 12b) of the secondary BF separator 12, and a secondary BF separation process is performed by the secondary BF separator 12. It should be noted that the content of the secondary BF separation process is similar to that of the primary BF separation process. Through the secondary BF separation process, the R3 reagent containing the labeled antibody that is unreacted and the cleaning solution are removed from the cuvette, and the complexes each composed of the magnetic particles, the antigen, and the labeled antibody remain in the cuvette C.

After the secondary BF separation process ends, the cuvette C is transferred to the setting part 18 by the transfer arm 12a (the catcher 12b) of the secondary BF separator 12, and the process is advanced to step S7.

In step S7, dispensing of the R4 reagent is performed by the R4/R5 reagent dispenser 40. That is, as shown in FIG. 4, through the movement of the moving unit 20, the catcher 21 grips the cuvette C at the setting part 18, and transfers the cuvette C to the dispensing position of the dispensing nozzle 42 (position directly beneath the nozzle). Then, the R4 reagent is discharged into the cuvette C from the dispensing nozzle 42, by a predetermined amount (50 μL). It should be noted that the cuvette C is kept gripped by the catcher 21, from when it is gripped by the catcher 21 of the moving unit 20 in step S7 until it is returned to the reaction part 9 in step S14 described below.

After the R4 reagent has been dispensed, as shown in FIG. 10, the liquid in the cuvette C is agitated by the agitation motor 23 of the catcher 21 being driven in step S8, and the magnetic particles accumulated in the bottom of the cuvette C are dispersed in the liquid.

Next, in step S9, as shown in FIG. 4, through the movement of the moving unit 20, the cuvette C held by the catcher 21 is transferred to the dispensing position of the dispensing nozzle 43 (position directly beneath the nozzle). Then, the R5 reagent is discharged into the cuvette C from the dispensing nozzle 43, by a predetermined amount (100 μL). As a result, the cuvette C contains a liquid (R4/R5 reagent) by about 150 μL. Different from the case where the R4 reagent is dispensed (step S7), the agitation operation of the measurement specimen is not performed between the R5 reagent dispensing in step S9 and the next step S10, but is performed in step S13 after an abnormality detection process in step S10 ends.

As shown in FIG. 10, after the R5 reagent is dispensed, determination (the abnormality detection process) whether the amount of the liquid (R4/R5 reagent) in the cuvette C is within a predetermined normal range is performed in step S10. Details of the abnormality detection process will be described later. As a result of the determination, with respect to a cuvette for which it has been determined that the amount of the liquid in the cuvette C is outside the normal range (abnormal amount), the "abnormality flag" is set on the measurement program.

After the abnormality detection process in step S10, in step S11, the CPU 4a determines whether abnormality has been detected (there is abnormality) in the amount of the liquid (R4/R5 reagent) in the cuvette C. When it has been determined that the liquid amount is within the normal range, the process is advanced to step S13. On the other hand, when it has been determined that there is abnormality, the process is advanced to step S12, and the CPU 4a outputs error information. As a result, notification message "R4/R5 constant amount abnormality" is displayed on the display unit 4b of the control apparatus 4, whereby abnormality notification to the user is performed.

In step S13, the liquid in the cuvette C is agitated by the agitation motor 23 of the catcher 21 being driven. Then, in step S14, the cuvette C gripped by the catcher 21 is returned to the reaction part 9 through the movement of the moving unit 20.

In step S15, the cuvette C is transported by the rotation of the reaction part 9, and the cuvette C is taken out of the reaction part 9 by the catcher 17a of the cuvette transfer part 17 at a predetermined taking-out position. Then, transfer of the cuvette C toward the measurement unit 14 is started by the catcher 17a being moved.

At this time, in step S16, it is determined whether the cuvette C being transferred is a cuvette C for which it has been determined that "there is abnormality". When it has been determined that the liquid amount is within the normal range in step S10 (when the abnormality flag is not set), the process is advanced to step S17. In step S17, the cuvette C gripped by the catcher 17a is set in the measurement unit 14, and the measurement process is performed by the measurement unit 14 on the measurement specimen in the cuvette C. After the measurement, in step S18, the cuvette C is taken out of the measurement unit 14 by the catcher 17a, and is discarded into the disposal part 17b. Then, in step S19, a measurement result obtained by the measurement unit 14 is outputted to the control apparatus 4.

On the other hand, in step S16, when the abnormality flag has been set for the cuvette C gripped by the catcher 17a, it is determined that it is a cuvette C having abnormality, and the process is advanced to step S18. That is, the cuvette C having abnormality is not subjected to the measurement process, and is discarded into the disposal part 17b. In this case, in step S19, information indicating that the measurement process was not performed due to an R4/R5 constant amount abnormality error (there is no measurement result) is outputted to the control apparatus 4.

In this manner, the measurement process operation by the immune analyzer 1 (the measurement mechanism unit 2) is performed.

Next, with reference to FIG. 8 to FIG. 11, the abnormality detection process (subroutine) of step S10 shown in FIG. 10 will be described.

The abnormality detection process is a process of determining whether the amount of the liquid in the cuvette C is within a predetermined range, based on an output from the detector 50 (the photoreceiver 52) during the movement (ascending movement) of the cuvette C relative to the detector 50.

Figure 11:
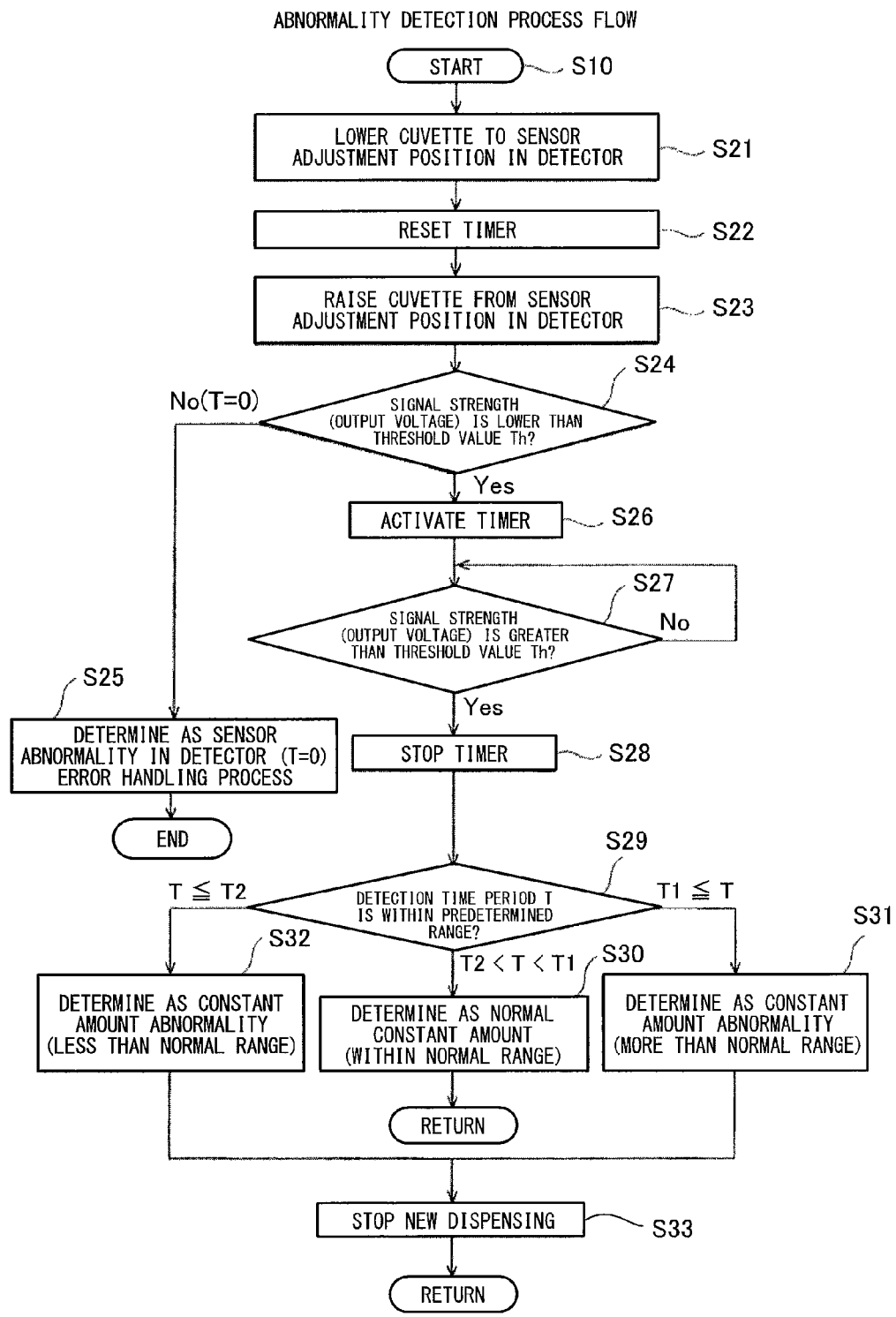
FIG. 11 is a flow chart for explaining an abnormality detection process (subroutine) in the measurement process operation shown in FIG. 10.

The abnormality detection process is started with the catcher 21 (cuvette C) located at the origin position Po, above the detector 50, as a result of the movement of the moving unit 20. As shown in FIG. 11, in step S21, the cuvette C is caused to descend to the sensor adjustment position Pb of the hole portion 53 in the detector 50, through movement in the Z-axis direction of the catcher 21. During this descending operation, the moving unit 20 (the Z-axis motor 35a) is driven under the descending movement condition shown in FIG. 9.

Upon the cuvette C reaching the sensor adjustment position Pb, the controller 2a resets a timer for measuring the detection time period T in step S22.

Then, in step S23, through movement in the Z-axis direction of the catcher 21, the cuvette C is caused to ascend from the sensor adjustment position Pb of the detector 50. During this ascending operation, the moving unit 20 (the Z-axis motor 35a) is driven under the ascending movement condition shown in FIG. 9. That is, in the detection area from the position p1 to the position p3 shown in FIG. 8, the catcher 21

(cuvette C) ascends at the constant speed v3 based on the ascending movement condition.

As shown in FIG. 11, after the ascent is started, in step S24, the controller 2a determines whether a signal strength (output voltage) from the photoreceiver 52 is lower than the threshold value Th (see FIG. 8).

When the liquid surface has passed the sensor position Ps and the signal strength becomes lower than the threshold value Th, the process is advanced to step S26, and the timer of the controller 2a is activated (measurement of time period T is started).

On the other hand, when the output voltage does not become lower than the threshold value Th during a predetermined time period (when T=0), the process is advanced to step S25.

In this case, there is a possibility that a signal output from the photoreceiver 52 is not normal. Therefore, in step S25, the controller 2a determines that there is sensor abnormality in the detector 50, and a predetermined error handling process is performed. For example, error information is outputted to the control apparatus 4, and the display unit 4b displays an error (sensor abnormality) and an indication that checking and maintenance are necessary. Further, in this case, the measuring operation is stopped.

When the timer is normally activated in step S26 (when the output voltage has become lower than the threshold value Th), the controller 2a determines whether the output voltage has become greater than the threshold value Th in step S27.

When the output voltage has become greater than the threshold value Th, the timer of the controller 2a is stopped in step S28. As a result, the controller 2a obtains the detection time period T, which is the time period while the output voltage was lower than the threshold value Th, that is, the time period from when the output voltage became lower than the threshold value Th (from when the timer was activated) until it became greater than the threshold value Th (till the timer was stopped).

In step S29, the CPU 4a receives the detection time period T from the controller 2a, and determines whether the detection time period T is within a predetermined time period range. That is, the obtained detection time period T is compared with the upper limit time period T1 and the lower limit time period T2.

As a result, when the detection time period T is within the detection time period range (T2<T<T1) between the lower limit time period T2 and the upper limit time period T1, the process is advanced to step S30, and it is determined that the amount of the liquid in the cuvette C is within the normal range (that is, the amount of the R4 reagent and the R5 reagent is normal). Then, the process is retuned to step S11 in the main routine.

On the other hand, when the detection time period T is longer than or equal to the upper limit time period T1 (when T1≤T) in step S29, the process is advanced to step S31. In this case, in step S31, the CPU 4a determines that there is constant amount abnormality in which the amount of the liquid in the cuvette C is greater than or equal to the upper limit amount (more than the normal range). As a result, the abnormality flag is set for the cuvette C to be detected, and the process is advanced to step S33.

Further, when the detection time period T is shorter than or equal to the lower limit time period T2 (when T≤T2) in step S29, the process is advanced to step S32. In this case, in step S32, the CPU 4a determines that there is constant amount abnormality in which the amount of the liquid in the cuvette C is less than or equal to the lower limit amount (less than the normal range). As a result, the abnormality flag is set for the cuvette C to be detected, and the process is advanced to step S33.

Then, in step S33, the CPU 4a transmits to the controller 2a an instruction to stop new dispensing operations thereafter, based on the determination result indicating the constant amount abnormality (step S31 or step S32). It should be noted that the new dispensing operations include not only the dispensing operation performed by the dispenser 40 to dispense the R4 and R5 reagents, but also the dispensing operation performed by the sample dispensing arm 5 to dispense the sample, the dispensing operation performed by the R1 reagent dispensing arm 6 to dispense the R1 reagent, the dispensing operation performed by the R2 reagent dispensing arm 7 to dispense the R2 reagent, and the dispensing operation performed by the R3 reagent dispensing arm 8 to dispense the R3 reagent. Then, the process is returned to step S11 in the main routine.

As a result, an error indication of constant amount abnormality is outputted in step S11 and step S12 in FIG. 10 based on the abnormality determination. Further, until the cuvette C for which the abnormality flag has been set is transferred to the measurement unit 14 (step S15) and is discarded based on the abnormality flag (step S18), the measuring operation by the measurement unit 14 is continued. Therefore, in the case where the abnormality determination has been made, with respect to each of cuvettes C that have been determined therebefore as having the normal constant amount, it is determined that there is no abnormality (without the abnormality flag) in step S16, and thus, the measurement process by the measurement unit 14 is performed.

Regarding the determination of the constant amount abnormality (step S31 or step S32), different causes for abnormalities are conceivable between the case where the liquid amount is greater than or equal to the upper limit amount (step S31), and the case where the liquid amount is less than or equal to the lower limit amount (step S32).

Specifically, when the liquid amount is greater than or equal to the upper limit amount (step S31), a conceivable cause is that the dispensed amount of one or both of the R4 and R5 reagents were excessive (abnormality in the R4/R5 reagent dispenser 40) or that there was abnormality in aspiration of the cleaning solution in the secondary BF separation process before the R4 and R5 reagents were dispensed (the aspiration was not enough and the cleaning solution remained in the cuvette C).

When the liquid amount is less than or equal to the lower limit amount (step S32), a conceivable cause is, for example, that the dispensed amount of one or both of the R4 and R5 reagents was insufficient or dispensing thereof was impossible (abnormality in the R4/R5 reagent dispenser 40) or that the amount of light from the light source 51 of the detector 50 was reduced. In this manner, by individually making determination for the case where the liquid amount is greater than or equal to the upper limit amount and for the case where the liquid amount is less than or equal to the lower limit amount, it is possible to deduce the cause of the abnormality in accordance with the content of the constant amount abnormality. Thus, checking and maintenance can be easily performed.

In the present embodiment, as described above, the detector 50 which includes the light source 51 and the photoreceiver 52, and the moving unit 20 which causes the cuvette C and the detector 50 to move relative to each other in the up-down direction are provided, and in addition, the controller 2a and the CPU 4a are provided which determine whether the amount of the liquid (R4/R5 reagent) in the cuvette C is within a predetermined range, based on an output from the detector 50 during the relative up-down movement between the cuvette C and the detector 50 caused by the moving unit 20. Accordingly, the output from the detector 50 during the relative up-down movement between the cuvette C and the detector 50 reflects the amount of the liquid contained in the cuvette C. Thus, not only the presence or absence of the liquid in the cuvette C, but also the amount of the liquid contained in the cuvette C can be obtained based on the output from the detector 50. Accordingly, it is possible to determine whether the amount of the liquid in the cuvette C is within the predetermined range.

Further, in the present embodiment, as described above, it is configured such that a sample and reagents are dispensed in a cuvette C and a measurement specimen is prepared in the cuvette C, and also the measurement unit 14 is provided which measures the measurement specimen in the cuvette C. Accordingly, a variation of the dispensed amounts tends to affect the measurement result. Thus, with respect to the cuvette C in which the measurement specimen is prepared, for which it is highly necessary to determine whether the liquid amount is within the predetermined range, it is possible to determine whether the liquid amount is within the predetermined range.

Further, in the present embodiment, as described above, it is determined whether the liquid amount of the R4 and R5 reagents is within the predetermined range. Accordingly, it is possible to determine whether the liquid amount of the R4 and R5 reagents in the cuvette C, a variation of dispensed amounts of the R4 reagent and the R5 reagent greatly affecting the analysis result, is within the predetermined range.

Further, in the present embodiment, as described above, the controller 2a and the CPU 4a are configured to determine whether the amount of the liquid (R4/R5 reagent) in the cuvette C is within the predetermined range (142.5 µL<liquid amount<157.5 µL), based on a signal strength (output voltage) that corresponds to the amount of light received by the photoreceiver 52. There occurs a difference in the amounts of light received by the photoreceiver 52, between the case where the light source 51 emits light to the liquid in the cuvette C and the case where the light source 51 emits light to the internal space in the cuvette C having no liquid therein. Thus, based on the output voltage that corresponds to the amount of light received by the photoreceiver 52, it is possible to accurately determine whether the amount of the liquid (R4/R5 reagent) in the cuvette C is within the predetermined range.

Further, in the present embodiment, as described above, the controller 2a and the CPU 4a are configured to determine whether the amount of the liquid in the cuvette C is within the predetermined range, based on whether the detection time period T, during which the signal strength (output voltage) that corresponds to the amount of transmitted light received by the photoreceiver 52 is lower than the threshold value Th, is within the predetermined detection time period range (T2<T<T1). Accordingly, the detection time period T during the ascent of the cuvette C relative to the detector 50 reflects the amount of the liquid in the cuvette C. Therefore, based on whether the detection time period T is within the predetermined detection time period range, it is possible to easily and accurately determine whether the amount of the liquid is within the predetermined range.

Further, in the present embodiment, as described above, the controller 2a and the CPU 4a are configured to determine, when the length of the detection time period T is longer than or equal to the upper limit time period T1 (T1≤T), that the amount of the liquid in the cuvette C is more than the predetermined range. Accordingly, when the length of the detection time period T is longer than or equal to the upper limit time period T1, it is known that the amount of the liquid in the cuvette C is greater than or equal to the upper limit amount. Thus, it is possible to easily and accurately determine whether the amount of the liquid is more than the predetermined range.

Further, in the present embodiment, as described above, the controller 2a and the CPU 4a are configured to determine, when the length of the detection time period T is shorter than or equal to the lower limit time period T2 (T≤T2), that the amount of the liquid in the cuvette C is less than the predetermined range. Accordingly, when the length of the detection time period T is shorter than or equal to the lower limit time period T2, it is known that the amount of the liquid in the cuvette C is less than or equal to the lower limit amount. Thus, it is possible to easily and accurately determine whether the amount of the liquid is less than the predetermined range.

Further, in the present embodiment, as described above, the controller 2a and the CPU 4a are configured to determine, when the detection time period T is 0 (T=0), that there is abnormality in the detector 50. Accordingly, it is possible to quickly detect abnormality in the detector 50, as well as to determine whether the amount of the liquid in the cuvette C is within the predetermined range.

Further, in the present embodiment, as described above, the controller 2a and the CPU 4a are configured to perform, when determining that the amount of the liquid in the cuvette C is not within the predetermined range, control to stop the next dispensing operation and thereafter. When the amount of the liquid in the cuvette C is not within the predetermined range, abnormality in the dispenser 40, abnormality in aspiration of the cleaning solution in the secondary BF separation process, reduction of the amount of light from the light source 51, and the like are conceivable. Thus, by stopping the next dispensing operation and thereafter, it is possible to quickly perform checking and the like of the dispenser 40, the secondary BF separator 12, and the light source 51.

Further, in the present embodiment, as described above, the controller 2a and the CPU 4a are configured to control, when determining that the amount of the liquid (R4/R5 reagent) in the cuvette C is not within the predetermined range (constant amount abnormality), the measurement unit 14 so as to perform the measurement process on the liquid in each of cuvettes C that have been determined therebefore as having the normal constant amount (without the abnormality flag). Accordingly, even when the next dispensing operation and thereafter are stopped based on the determination of the dispensing abnormality, it is possible to perform the measurement process on the cuvettes C which each have been determined as having the normal constant amount. Therefore, it is possible to suppress the measurement specimen from being wasted when abnormality has occurred.

Further, in the present embodiment, as described above, the controller 2a and the CPU 4a are configured to perform, when determining that the amount of the liquid in the cuvette C is not within the predetermined range, control to make notification of abnormality. In this configuration, when the amount of the liquid in the cuvette C is not within the predetermined range, the operator is notified of the abnormality, and thus, the operator can quickly take measures such as checking.

Further, in the present embodiment, as described above, the moving unit 20 is configured to move the cuvette C in the up-down direction relative to the detector 50 which is fixedly set. Accordingly, it is only necessary to move the cuvette C, and thus, when compared with the case where the detector 50 is moved, it is possible to easily cause the cuvette C and the detector 50 to move relative to each other.

Further, in the present embodiment, as described above, the moving unit 20 is configured such that while the catcher 21 continues gripping the cuvette C, the dispenser 40 dispenses the R4 reagent and the R5 reagent into the cuvette C and the cuvette C is moved in the up-down direction relative to the detector 50. Accordingly, it is possible to perform the dispensing operation and the detection operation while the catcher 21 continues gripping the cuvette C, and thus, it is possible to simplify the structure of the apparatus and to improve the process efficiency. Further, since the same cuvette C is kept gripped until the dispensing and detection operations are completed, it is possible to prevent malfunction such as gripping another cuvette C during the operations.

Further, in the present embodiment, as described above, the controller 2a and the CPU 4a are configured to determine whether the amount of the liquid in the cuvette C is within the predetermined range, based on an output from the detector 50 during the period in which the moving unit 20 is causing the cuvette C to ascend at a constant speed (speed v3) relative to the detector 50. Accordingly, it is not necessary to take into consideration of acceleration and deceleration in the relative movement between the cuvette C and the detector 50 during the detection operation, and thus, it is possible to easily determine whether the amount of the liquid is within the predetermined range.

Further, in the present embodiment, as described above, the agitation motor 23 is configured to agitate the liquid in the cuvette C (step S13), after the R5 reagent was dispensed in step S9, the moving unit 20 caused the cuvette C to ascend relative to the detector 50, and the detector 50 performed detection. When agitation is performed before the detection, a variation may occur in determination of the amount of the liquid in the cuvette C because some of the liquid in the cuvette C is attached to the internal wall of the cuvette C whereby the position of the liquid surface is varied. However, as in the present embodiment, by performing agitation after the detection, it is possible to prevent a variation from occurring in determination of the amount of the liquid in the cuvette C.

It should be noted that the embodiment disclosed herein is merely illustrative in all aspects and should not be considered as being restrictive. The scope of the present invention is defined not by the description of the above embodiment but by the scope of the claims, and includes meaning equivalent to the scope of the claims and all modifications within the scope.

For example, the above embodiment has shown an example in which the analyzer according to the present invention is applied to the immune analyzer 1. However, the present invention is not limited thereto. The present invention can be applied to any analyzer that dispenses a constant amount of a liquid, and to analyzers other than immune analyzers.

Further, the above embodiment has shown an example in which the liquid amount of the R4 reagent and the R5 reagent is determined. However, the present invention is not limited thereto. The present invention may determine the liquid amount of the R1 to R3 reagents, a sample, and the like. Further, in the present invention, other than a sample and the reagents, any liquid (such as the cleaning solution) whose amount is to be determined may be used.

Further, the above embodiment has shown an example in which the amount of the liquid dispensed into a cuvette C is determined. However, the present invention is not limited thereto. In the present invention, other than a cuvette, any container into which a liquid is dispensed may be used.

Further, the above embodiment has shown an example in which the photoreceiver is configured to receive light that has been transmitted through a cuvette. However, the present invention is not limited thereto. In the present invention, the photoreceiver may be configured to receive light reflected at a liquid in a cuvette or scattered light.

Further, the above embodiment has shown an example in which it is configured such that the amount of the liquid in a cuvette is determined based on an output from a detector during the ascent of the cuvette relative to the detector. However, the present invention is not limited thereto. In the present invention, it may be configured such that the amount of the liquid in the cuvette is determined based on an output from the detector during the descent of the cuvette relative to the detector.

Further, the above embodiment has shown an example in which it is configured such that the detector is fixedly provided and a cuvette is moved (ascends) relative to the detector. However, the present invention is not limited thereto. In the present invention, the detector may be moved in the up-down direction relative to a cuvette that is fixedly held, or both of the cuvette and the detector may be moved in the up-down direction.

Further, the above embodiment has shown an example in which it is configured such that a cuvette (catcher) is caused to ascend at the constant speed v3 during the liquid amount detection operation. However, the present invention is not limited thereto. In the present invention, the cuvette (catcher) may be accelerated or decelerated during the liquid amount detection operation. In this case, it is sufficient that the upper limit time period T1 and the lower limit time period T2 are set in consideration of the change in the movement speed.

Further, the above embodiment has shown an example in which a cuvette which has been determined as having an abnormal liquid amount and for which the abnormality flag has been set is not subjected to the measurement process by the measurement unit and is discarded into the disposal part. However, the present invention is not limited thereto. In the present invention, it may configured such that the measurement process is performed also on the cuvette for which the abnormality flag has been set, and the measurement result and an error indicating that the measurement specimen has been determined as having constant amount abnormality are outputted.

Further, the liquid amounts of the R4 reagent and the R5 reagent and the specific numerical values such as the upper limit amount and the lower limit amount described in the above embodiment are merely an example, and the present invention is not limited thereto. The upper limit amount is set as a value that allows normal measurement to be performed. If the liquid in the cuvette C is spilt due to the agitation operation in step S13, the antigen contained in the sample bound to the labeled antibody is lost, and accurate measurement cannot be performed. Therefore, specifically, the upper limit amount is set to an amount that would prevent from the liquid in the cuvette C from spilling even if the agitation operation is performed on the cuvette C in step S13. The lower limit amount is set to a value that allows normal measurement to be performed. Specifically, the lower limit amount is set to an amount that allows determination that the R5 reagent has been dispensed when the R4 reagent was already dispensed. That is, in the present invention, the lower limit amount may be set to a value greater than the dispensing amount of the R4 reagent.

Further, in the above embodiment, the controller 2a performs step S1 to step S9, step S13 to step S19, and step S21 to step S28 of step S10, and the CPU 4a performs step S11, step S12, and step S29 to step S33 of step S10. However, the present invention is not limited thereto. In the present invention, the CPU 4a may perform step S1 to step S19 and step S21 to step S33 of step S10.

What is claimed is:

1. An analyzer for analyzing a substance in a container comprising:
    a dispenser configured to dispense a liquid into the container;
    a detector that includes phototransmitter and a photoreceiver, wherein the phototransmitter is configured to emit light into the container and the photoreceiver is configured to receive light emitted from the phototransmitter, wherein liquid is determined to be detected based on an amount of light received at the photoreceiver;
    a moving unit configured to move one of the container and the detector relative to the other during a detection time to facilitate detecting a presence of liquid within the container at a plurality of positions within the container; and
    a controller configured to determine whether an amount of the liquid in the container is within a predetermined range based on the detected presence of liquid within the container the plurality of positions, wherein
    the controller determines that the amount of the liquid in the container is within the predetermined range in response to determining that a time period of the detection time during which liquid is detected by the detector is within a predetermined detection time period range.

2. The analyzer according to claim 1, wherein
    the controller determines whether the amount of the liquid in the container is within the predetermined range, based on outputs from the detector during a period in which the moving unit is causing the container and the detector to move relative to each other.

3. The analyzer according to claim 1, wherein
    the container is a reaction container into which a sample dispensed from a sample container containing the sample and a reagent dispensed from a reagent container containing the reagent are mixed together to prepare a measurement specimen, and
    the analyzer further comprises a measurement unit which measures the measurement specimen in the reaction container.

4. The analyzer according to claim 1, wherein the liquid corresponds to a sample or a reagent.

5. The analyzer according to claim 1, wherein
    the controller determines that the amount of the liquid in the container is more than the predetermined range when a time period of the detection time during which liquid is detected by the detector is longer than or equal to an upper limit time period of the predetermined detection time period range.

6. The analyzer according to claim 1, wherein
    the controller determines that the amount of the liquid in the container is less than the predetermined range when a time period of the detection time during which liquid is detected by the detector is shorter than or equal to a lower limit time period of the predetermined detection time period range.

7. The analyzer according to claim 1, wherein
    the controller is configured to determine an abnormality in the detector when the time period of the detection time during which liquid is detected by the detector is 0.

8. The analyzer according to claim 1, wherein
    the controller is configured to control the dispenser to not dispense the liquid into a next container when the controller has determined that the amount of the liquid in the first container is outside of the predetermined range.

9. The analyzer according to claim 8, wherein
    the container is a reaction container into which a sample and a reagent are dispensed to prepare a measurement specimen,
    the analyzer further comprises a measurement unit which measures the measurement specimen in the reaction container, and
    the controller is configured to control, when determining that an amount of the measurement specimen in the reaction container is not within the predetermined range, the measurement unit so as to perform a measurement process on a measurement specimen in a reaction container whose amount has been determined there before as being within the predetermined range.

10. The analyzer according to claim 1, wherein
    the controller is configured to trigger a notification to indicate an abnormality when the controller has determined that the amount of the liquid in the container is not within the predetermined range.

11. The analyzer according to claim 1, wherein
    a position of the detector is fixed within the analyzer, and
    the moving unit is configured to move the container in a vertical direction relative to the detector.

12. The analyzer according to claim 11, wherein
    the moving unit includes a grip portion configured to grip the container, and
    the dispenser is controlled to dispense the liquid into the container while the moving unit grips the container and moves the container vertically relative to the detector.

13. The analyzer according to claim 2, wherein
    the controller is configured to determine whether the amount of the liquid in the container is within the predetermined range, based on outputs from the detector during a period in which the moving unit is causing the container and the detector to move relative to each other at a substantially constant speed.

14. The analyzer according to claim 1, further comprising:
    an agitator which agitates the liquid in the container, wherein
    the agitator is configured to agitate the liquid in the container after the moving unit has caused the container and the detector to move relative to each other and the detector has performed detection.

15. The analyzer according to claim 3, wherein
    the reagent includes a first reagent and a second reagent,
    the reagent container includes a first reagent container containing the first reagent and a second reagent container containing the second reagent,
    the dispenser dispenses the first reagent from the first reagent container into the reaction container, and dispenses the second reagent from the second reagent container into the reaction container, and
    the controller is configured to cause the moving unit to cause the reaction container in which the first reagent and the second reagent have been dispensed and the detector to move relative to each other, to allow the detector to perform detection.

16. The analyzer according to claim 1, wherein
    the phototransmitter emits light to a lateral face of the container.

* * * * *

UNITED STATES PATENT AND TRADEMARK OFFICE
CERTIFICATE OF CORRECTION

PATENT NO. : 9,228,946 B2
APPLICATION NO. : 13/738635
DATED : January 5, 2016
INVENTOR(S) : Kazutoshi Tokunaga et al.

Page 1 of 1

It is certified that error appears in the above-identified patent and that said Letters Patent is hereby corrected as shown below:

In the Claims

In column 19, claim 1, line 10, after "a detector that includes" insert --a--.

In column 19, claim 1, line 24, before "the plurality of positions," insert --at--.

Signed and Sealed this
Fifth Day of July, 2016

Michelle K. Lee
*Director of the United States Patent and Trademark Office*